(12) United States Patent
Los

(10) Patent No.: US 9,308,212 B2
(45) Date of Patent: Apr. 12, 2016

(54) COMPOSITIONS COMPRISING ALPRAZOLAM FOR TREATING PRIMARY INSOMNIA AND INSOMNIA ASSOCIATED WITH ANXIETY STATES AND PROCESS FOR PREPARING THEM

(71) Applicant: LABORATORIOS BAGO S.A., Buenos Aires (AR)

(72) Inventor: Mario Atilio Los, Buenos Aires (AR)

(73) Assignee: LABORATORIOS BAGO S.A., Buenos Aires (AR)

( * ) Notice: Subject to any disclaimer, the term of this patent is extended or adjusted under 35 U.S.C. 154(b) by 32 days.

(21) Appl. No.: 14/102,934

(22) Filed: Dec. 11, 2013

(65) Prior Publication Data

US 2014/0107108 A1 Apr. 17, 2014

Related U.S. Application Data

(63) Continuation of application No. 12/363,802, filed on Feb. 2, 2009, now abandoned.

(30) Foreign Application Priority Data

Feb. 5, 2008 (EP) .................................. 08002077

(51) Int. Cl.
*A61K 31/5517* (2006.01)
*A61K 9/00* (2006.01)
*A61K 9/20* (2006.01)

(52) U.S. Cl.
CPC ............. *A61K 31/5517* (2013.01); *A61K 9/006* (2013.01); *A61K 9/2027* (2013.01); *A61K 9/2054* (2013.01); *A61K 9/2095* (2013.01)

(58) Field of Classification Search
None
See application file for complete search history.

(56) References Cited

U.S. PATENT DOCUMENTS

2005/0244517 A1* 11/2005 Hall et al. ..................... 424/733
2006/0134200 A1* 6/2006 Vandoni et al. ............... 424/464

FOREIGN PATENT DOCUMENTS

MX PA01004963 A 8/2003

OTHER PUBLICATIONS

Ringdahl, et al, Treatment of Primary Insomnia, JABFP, May-Jun. 2004, pp. 212-219, vol. 17, No. 3.
Walsh, Drugs Used to Treat Insomnia in 2002: Regulatory-Based Rather Than Evidence-Based Medicine, Sleep, 2004, pp. 1441-1442, vol. 27, No. 8, St. Louis, Missouri.
Boceta Osuna Jalme, et al., Control of Neuropsychological Symptoms, Atencion Primaria/Sociedad Espanola De Medicina De Familia Y Comunitaria, Nov. 1, 2006, pp. 1-37, vol. 38, Suppl. 2.
Bredenberg, et al., In Vitro and In Vivo Evaluation of a New Sublingual Tablet System for Rapid Oromucosal Absorption Using Fentanyl Citrate As the Active Substance, European Journal of Pharmaceutical Sciences 20, 2003, pp. 327-334.
Scavone, et al., Alprazolam Kinetics Following Sublingual and Oral Administration, J. Clin. Psychopharmacology, Oct. 1987, pp. 332-334, vol. 7, No. 5.
Scavone, et al., The Pharmacokinetics and Pharmacodynamics of Sublingual and Oral Alprazolam in the Post-Prandial State, Eur. J. Clin. Pharmacol. (1992) 42, pp. 439-443.

\* cited by examiner

*Primary Examiner* — Svetlana M Ivanova
(74) *Attorney, Agent, or Firm* — Dinsmore & Shohl LLP

(57) ABSTRACT

Disclosed is a composition comprising alprazolam for treating primary insomnia and insomnia associated with anxiety states and the corresponding use and method comprising the administration of alprazolam sublingual tablets having a disintegration time lower than 30 seconds and having the alprazolam preferably in non-crystalline or partially crystalline form according to the X-ray diffraction crystallography expanded for the position delta 9-12.5 (2 theta), to a patient suffering from said disorder. There is also disclosed a method for preparing a composition according to the invention, where the alprazolam is solved in a pharmaceutical acceptable solvent and a binder, preferably polyvinylpyrrolidone, is incorporated to the solution. A pre-made mixture of part of the cross-linked carboxymethyl-cellulose and the rest of the ingredients of the composition is impregnated with the solution and is dried and grinded, and is added to the rest of the cross-linked carboxymethyl-cellulose and the flavoring additives, being then mixed and compressed.

12 Claims, 3 Drawing Sheets

COMPOSITIONS COMPRISING ALPRAZOLAM FOR TREATING PRIMARY INSOMNIA AND INSOMNIA ASSOCIATED WITH ANXIETY STATES AND PROCESS FOR PREPARING THEM

CROSS-REFERENCE TO RELATED APPLICATIONS

This application is a continuation of U.S. patent application Ser. No. 12/363,802 filed Feb. 2, 2009, which claims priority of European Patent Application 08002077.9 filed Feb. 5, 2008.

FIELD OF THE INVENTION

The present invention refers to a method for treating patients suffering from primary insomnia and insomnia associated with anxiety states and a sublingual pharmaceutical composition containing alprazolam as the active principle useful for the treatment of primary insomnia and insomnia associated with anxiety states. The invention also describes the elaboration procedure of the composition and the features of the obtained sublingual or oral tablets. The invention further refers to the use of alprazolam and/or a composition comprising alprazolam for the manufacture of a medicament for the treatment of primary insomnia by sublingual administration.

BACKGROUND ART

Sleeping is a physiological process which is controlled by two biological processes, the homeostatic mechanism and the circadian rhythm. Most adults need about eight hours average of sleeping each night, on a regular basis, in order to feel rested and alert during the daytime. Any change in this routine disrupts the delicate balance between two processes that interact to regulate sleeping. The homeostatic mechanism manifests itself as a growing impulse towards sleeping that accumulates through the alert period, typically during the daytime, and fades away through the sleeping period. The circadian rhythm operates as a 24-hour internal clock; as a part of this cyclic process, the body releases hormones, such as melatonin, in order to help the individual know when is the right time to sleep and to wake. The sleeping-wakefulness circadian rhythm shows a biphasic curve with the greater impulse toward sleeping occurring between midnight and 5 A.M., and between 2 and 4 in the afternoon.

Many physiological functions are characterized by daytime rhythms, in which circulating hormone levels fluctuate during the daytime and/or nighttime. Certain clinical disorders, such as insomnia, are associated with abnormalities in these rhythms. The time of administration, within 24-hour periods, of drugs intended for prevention and treatment of such disorders may be a critical factor in the determination of the efficacy of therapy.

Insomnia is one of the most prevalent sleeping diseases and refers to a clinical condition, which lasts at least one month, of difficulties in conceiving sleeping, or keeping the sleeping state, of waking frequently during nighttime or very early in the morning or also to an unsuitable perception of sleeping. This precludes the recovery that the body needs during the nighttime rest, the possible consequences being daytime somnolence, low concentration, tiredness and disability to feel active during the day.

A study by the National Sleep Foundation of the United States in 2002 reported that 74% of American adults experiment problems in sleeping several nights a week or more, 39% sleep less than seven hours per night and 37% exhibit somnolence during the daytime, thus interfering with their daily activities.

In anxiety states the presence of associated insomnia is frequent. Specialists think that the prevalence of insomnia is also related to age and gender of individuals, the prevalence being higher in older individuals, especially adults older than 65, being women the most affected.

Primary insomnia is sleeplessness that is not attributable to a medical, psychiatric, or environmental cause.

In the United States, primary insomnia is diagnosed in approximately 15% of patients with insomnia who are referred to sleep disorder centers following exclusion of other predisposing conditions. Primary insomnia is estimated to occur in 25% of all patients with chronic insomnia.

Despite that the consequences associated with chronic insomnia remain debatable, the following associations have been noted:

increased risk of mortality is associated with short sleep lengths;

insomnia is the best predictor of the future development of depression;

catastrophic worry about the consequences of not sleeping is common among patients with chronic insomnia and serves to maintain the sleep disturbance;

increased risk exists of developing anxiety, alcohol and drug use disorders, and nicotine dependence;

poor health and decreased activity occur;

The ideal hypnotic or hypnophore is a drug that will induce sleeping in a quick, predictable fashion. It shall keep sleeping for a 7 to 8-hour period and avoid frequent awakenings. It must preserve sleep architecture with all its stages and must not induce adverse effects such as hang over (resaca matinal, in Spanish).

Early treatments for insomnia usually used central nervous system (CNS) depressants such as barbiturates. These compounds have shown a series of drawbacks. Due to their long half-life, they are typically long-acting (around 8-50 hours) and exhibit a largely known spectrum of side effects, including drowsiness, confusion, depression effects, and the next day hang over. Additionally, the chronic and wrong use of these compounds, i.e. without medical monitoring, has lead to physical and psychological dependence in some cases.

During the '80s, the pharmacological treatment of insomnia abruptly changed from barbiturates and other CNS depressants to the class of benzodiazepines of sedative-hypnotic effect. This kind of compounds produces a soothing effect, resulting in a state similar to sleeping in human beings and animals, with a greater safety range than previously used hypnotics. However, many benzodiazepines have side effects which limit their usefulness in certain populations of patients.

These problems include synergism with other CNS depressants (especially alcohol), development of tolerance with dose repetition, dependence, withdrawal, insomnia rebounding after dosing discontinuation, the effects of hang over the next day and weakening of psycho-motor functioning and memory. Somnolence on the next day and weakening of memory, which may include amnesia of events that occurred either before or after drug administration, are of special concern in elderly people, whose cognitive functions may already be damaged by the aging process.

In spite of the above, benzodiazepines have still been used for many decades and have become increasingly popular due to their low toxicity as compared to other drugs of similar action.

Diseases treated with benzodiazepines are a wide range of pathologies since they have several effects. The best known effects of benzodiazepines are as anticonvulsants, antipsychotic, muscle relaxants, sedatives and hypnotics. When benzodiazepines are used, some of their effects are desired with respect to the specific disorder treated, but others are considered side effects. Even at the dose levels used, for example against insomnia, the sedative effect of benzodiazepines may be a great disadvantage. Therefore, it is advantageous and important to find a form of administration of benzodiazepines which allows for application of the right and necessary dose to achieve the desired affect and which allows for better compliance of the patient. Some drugs which are only available as oral tablets or pills may be difficult to administer to elderly people and children, and hence it is of practical importance the availability of a pharmaceutical unit dosage form which disintegrates in a few seconds and whose active principle is absorbed through the sublingual and buccal mucosa of the patient.

Therefore, there is still a need to find a form of administration of benzodiazepines that is efficient and with a quick action onset in the treatment of primary insomnia or associated to anxiety states.

Alprazolam (28981-97-7) is a short-acting benzodiazepine described during 1970 in patents DE 2.012.190 (Sep. 24, 1970) and U.S. Pat. No. 3,987,052 (Oct. 19, 1976), which has demonstrated an interesting anxiolytic activity. However, it has not yet been approved for use in the short-term treatment of insomnia, neither in the United States nor in Europe.

Throughout the years, the search for new pharmaceutical forms containing alprazolam or new routes of administration different from the traditional pharmaceutical form (oral tablets) has been a subject of interest. Generally in order to reach the presence of alprazolam in blood in as little time as possible since the administration to the patient, thus assuring the quick start of the therapeutic effect.

Literature indicates that when the active ingredient is absorbed through the sublingual and buccal mucosas, such absorption allows for a rapid bioavailability thereof as the active ingredient directly enters the circulatory system, thus avoiding the gastrointestinal passage and the subsequent liver passage (S. Bredenberg et al (European Journal of Pharmaceutical Sciences 20 (2003) 327-334). Thus, in the recent years the patent literature mentions, among others, the following formulations.

Dugger III Harry et al. in US Patent Application 2004/0141923 AI (Jul. 22, 2004)) disclose a spray for buccal use containing alprazolam.

Although said document claims and describes generally a method for inducing sleep comprising spraying the oral mucosa of the patient with a "therapeutically effective amount" of the buccal spray containing alprazolam of the invention, it can be considered that such a statement is a mere expression of wish, because it lacks a technical basis. As a matter of fact, said document is totally silent as concerns the "application as a sleeping inductor" of alprazolam, there is no specific test supporting such a statement and, consequently, it is silent as concerns how much a "therapeutically effective amount" means in said treatment, there is no disclosure about the dosing in the treatment of insomnia. Moreover, in the specification alprazolam is described as being utilized for the treatment of anxiety and associated symptoms such as depression, dysthymic disorders such as "neurotic chronic" depression, panic attacks, agoraphobia and other phobias, obsessive-compulsive disorders, personality disorders.

Rabinowitz et al. (U.S. Pat. No. 6,737,048 B2 (May 18, 2004) and U.S. Pat. No. 7,060,255 B2 (Jun. 13, 2006)) disclose therapeutic forms containing alprazolam, among other benzodiazepines, for its administration by inhalation. However, both patents are not only silent as concerns suitable use and doses of alprazolam for the treatment of insomnia but rather advise the use thereof in situations wherein a sustained action of the medicament is desired, such as for example in panic attacks.

Los Mario in Mexican Patent MX 231185 (Oct. 10, 2005) and Argentine Patent Application (P000102422) published under number AR 32.585 (Nov. 19, 2003); discloses a procedure to prepare sublingual tablets containing alprazolam; useful for the treatment of panic attacks or acute anxiety episodes. This document is also silent as concerns the use of sublingual tablets as sleep inductors in primary insomnia or insomnia associated to anxiety states. In addition, at commercial scale, the procedure described therein has presented frequent practical problems of agglomeration during granulation.

Therefore, there still exists the need to provide a method for the treatment of insomnia comprising the administration of a benzodiazepine, preferably alprazolam; not having remarkably the side effects of benzodiazepines; in a suitable pharmaceutical form of easy disintegration and absorption which allows for quick start of action, and with a dosage and daily posology which allows the patient to comply the indicated treatment better.

SUMMARY OF THE INVENTION

Consequently, a major object of the present invention is to provide a pharmaceutical form for oral administration, preferably sublingual, of alprazolam, of rapid disintegration, rapid start of therapeutic action in the treatment of primary insomnia or associated with anxiety states and not having the disadvantages of benzodiazepines.

Another object of the present invention is to provide a form of administration of alprazolam for the treatment of primary insomnia or associated with anxiety states, which reduces to its minimum expression or avoids the first step of liver metabolism.

Another object of the present invention is to provide a form of administration of alprazolam having a beneficial clinical and pharmacological profile.

Another object of the present invention is to provide a form of administration of alprazolam for the treatment of primary insomnia or associated with anxiety states, which is superior to conventional routes of administration.

Another object of the present invention is to provide a new use of alprazolam or a composition comprising alprazolam for the manufacture of a medicament for treating primary insomnia by sublingual administration.

Another object of the present invention is a pharmaceutical composition in the form of sublingual tablets for the use according to the invention characterised by comprising the combination of alprazolam and a binder having mucoadhesive properties; wherein the ratio of alprazolam to the binder is in the range between 0.3:1 and 3:1.

Another object of the present invention is a process for preparing a pharmaceutical composition according to the invention, wherein the preparation procedure comprises the following steps:

dissolving alprazolam in a pharmaceutical acceptable solvent and incorporating the binder and impregnating with the solution formed a pre-made mixture of between 20% to 30%, preferably 25%, of cross-linked carboxymethylcellulose and the rest of the ingredients of the composition;

drying the above granular mass and grinding until uniform granulometry is achieved;

adding the rest of the cross-linked carboxymethyl-cellulose and the flavoring additives to the dry mass, then mixing and compressing.

Another objet of the invention is to provide a new use of a composition of alprazolam for the manufacture of a pharmaceutical composition according to the invention for treating anxiety states and for preventing panic attack.

Surprisingly, it has been found that it is possible to obtain small size and weight tablets containing small doses of alprazolam homogeneously distributed and having a disintegrating time that can be preferably lower than 1 minute, more preferably lower than 30 seconds, and still more preferably lower than 15 seconds and having desired solubility and bioavailability characteristics which allow for rapid start of action. Particularly, said tablets have shown to be effective in the treatment of primary insomnia or associated with anxiety states. In the short-time treatment of insomnia associated with anxiety states as will be described in more detail with respect to embodiment examples, alprazolam administered in sublingual tablets according to the present invention showed to be efficient in more than 90% of the patients who used it. Alprazolam sublingual tablets were clinically shown to be more efficient than oral tablets with the same alprazolam content, in reducing latency time in insomnia, in statistically significant terms.

BRIEF DESCRIPTION OF THE DRAWINGS

Other advantages and characteristics of the invention will become evident from the following description in which, entirely non-limitatively, are described some preferential embodiments of the invention, with reference to the appended drawings.

The figures show.

Figure 1:
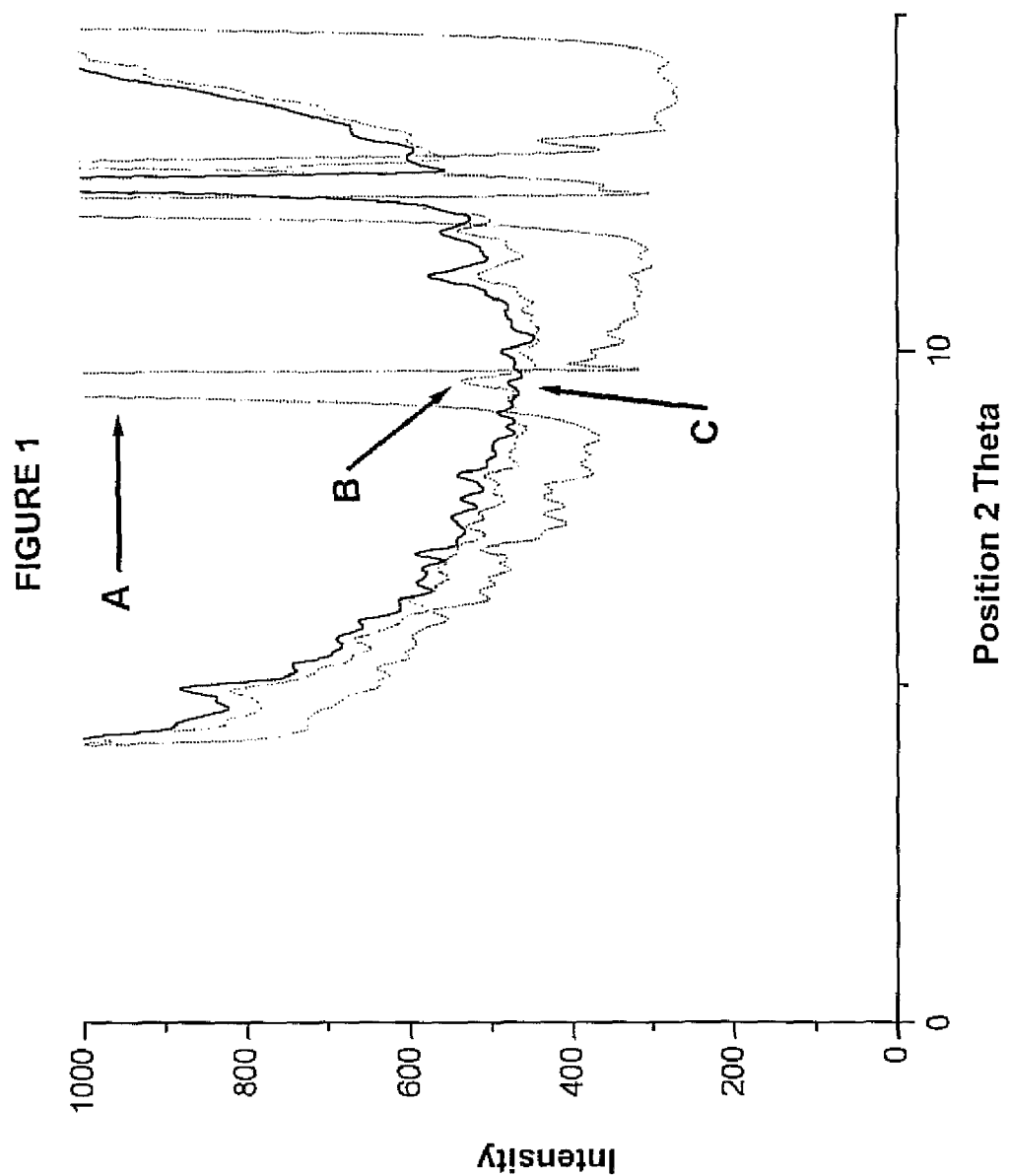
FIG. 1 describes X-ray diffraction graphs expanded for the Ia position Delta 9-12.5 (2 theta) corresponding to 3 different overlapped samples containing alprazolam.
Sample A: corresponds to pure.
Sample B: corresponds to the physical mixture of all components of the sublingual tablets, in the same proportion as used according to what is described in example 1 of the present invention.
Sample C: Corresponds to tablets with a content of 0.5 mg alprazolam made according to the procedure of Example 1, and ground.

Sample D: corresponds to tablets with the same alprazolam content (0.5 mg) prepared according to example 1, ground and submitted to a 36-month aging from its elaboration date, and ground.

DETAILED DESCRIPTION OF THE INVENTION

Administration of active principles for therapeutic use by sublingual route aims at achieving good absorption, high bioavailability and immediate therapeutic effect. It is an interesting route for the treatment of acute processes, and more convenient for the patient than the injectable form. However, there exist technical problems which do not make it always possible to dispose of this interesting administration route.

Technical and scientific literature also describes the importance of the amorphous form over the crystalline one in the absorption of scarcely soluble active principles. Thus, for instance:

U.S. Pat. No. 6,197,349 describes that amorphous novobiocine is 10 times more soluble than the crystalline form and is orally absorbed. It is known that solid crystalline substances have a defined form according to established crystallographic systems which they maintain even after fine grinding, as the arrangement of molecules in the lattice remains intact. Substances in their amorphous state do not have a defined structure, show irregularities in three dimensions, are thermodynamically less stable and confer the active principle its maximum solubility.

Grinding or milling increases the surface of the active principle, but does not change its crystallographic system, i.e. does not turn them into amorphous substances.

S. Bredenberg et al (European Journal of Pharmaceutical Sciences 20 (2003) 327-334) mention that the better sublingual absorption of pharmaceutical forms is associated with the following characteristics: 1) Disintegration rate of the tablet; 2) Dissolution time of its active principle, and in addition: 3) Contact time at the administration site.

If the contact time is short and absorption is incomplete, part of the pharmaceutical form or particles from the disintegration of the tablet will be swallowed and will notably affect the active principle's bioavailability.

The results obtained by researchers via the above mentioned works, indicate that the sublingual route is effectively an alternative worth exploring.

In 1987, Joseph Scavone, David Greenblatt and Richard Shader (J. Clin. Psychopharmacology—Vol. 7 No 5, October 1987) demonstrated in healthy volunteers treated with commercially available tablets for oral (buccal) administration, that sublingual absorption of alprazolam is possible. Such commercially available tablets maintained during 15 minutes under the tongue in volunteers with a previous 8-hour fasting and a 3-hour fasting following drug administration, showed that sublingual absorption was as fast as oral absorption under fasting and without a statistically significant difference.

In 1992, the same authors (J. M. Scavone, D. J. Greenblatt, J: E: Goddard, H. Friedman, J. S. Harmatz and R. I. Shader— EUR. J. CLIN. PHARMACOL. (1992) 42: 439-443) confirmed that post-prandial sublingual absorption by keeping the 1-mg tablet of alprazolam during 15 minutes under the tongue, was lower than the absorption previously obtained by the same authors in patients under fasting. In addition, they confirmed that after 15 minutes no residues from the tablets were detected under the tongue.

However, in the therapeutic field the use of an oral tablet that must be necessarily be kept under the tongue for 15 minutes in order to make it possible the absorption of its active principle is not of practical application.

It is well known that disintegration is a feature of significant importance for tablets intended for oral administration and even more relevant for sublingual tablets, since active principles are preferably absorbed in the buccal cavity through the buccal or sublingual mucosa. Also, it is well known that the greater the disintegration rate the faster the drug availability in the medium to be absorbed. For drugs of wide application in human therapy, different pharmacopoeias specify a maximum time for tablet disintegration in order to assure its efficacy. Thus, for example, Pharmacopeia USP XXIII requires for isosorbide dinitrate or nitroglycerine sublingual tablets a maximum disintegration time not greater than 2 minutes and for ergotamine tartrate, not higher than 5 minutes. It also mentions others with greater disintegration time. Said background references remark the practical importance of disintegration time directly associated with therapeutic activity and efficacy of each product.

The inventors have found that it is possible to obtain alprazolam sublingual tablets with the desired characteristics useful in the treatment of primary insomnia or associated with anxiety states by a simple, economical process. The elaboration procedure generally requires the following steps:

a) dissolve alprazolam in a pharmaceutically acceptable solvent;

b) afterwards dissolve in the above solution the binder having mucoadhesive properties in an amount by weight that is not higher than the alprazolam content thereof;

c) impregnate a pre-made mixture of 20% to 30%, preferably 25%, of cross-linked carboxymethyl-cellulose and the rest of the ingredients of the composition, with the above solution containing the active principle and the binder;

d) drying the obtained granulate under vacuum or in a fluidized bed dryer up to 50° C. in order to obtain a residual moisture level of 2.0 to 3.0%;

e) homogenizing the above granulate bypassing through a conical sieve (991 microns) and incorporate to the obtained granulate the rest of the cross-linked carboxymethyl-cellulose and the flavoring additives;

f) finally mixing, compressing and analyzing.

Most common binders are alginic acid, methyl-cellulose, gelatin, acacia gum, microcrystalline cellulose and polyvinylpyrrolidone. The binder of choice is polyvinylpyrrolidone.

Lubricants include magnesium stearate or sodium stearyl fumarate. Most preferred is sodium stearyl fumarate.

As diluents, lactose, microcrystalline cellulose, xylitol, mannitol or cross-linked carboxymethyl-cellulose (AC-DI-SOL) may be used. Preference is given to cross-linked carboxymethylcellulose.

Suitable flavorings are also employed.

The elaboration procedure of the tablets obtained according to the present invention and as indicated for illustrative purposes in the corresponding examples, has remarkable characteristics; among them the following are to be remarked:

Solid alprazolam (crystalline powder) is not directly mixed with the other components of the pharmaceutical composition. The previous dissolution of alprazolam in a solvent and subsequent impregnation of the excipients of the composition aids homogeneous distribution of the active principle throughout the mass of the excipients of the tablets. In an industrial level, this step helps assuring uniformity of the contents of the obtained tablets; the latter being an indispensable parameter of analytical control for products of pharmaceutical use.

Does not show the practical problems of agglomeration during granulation, possibly due to absence of stearic acid as a crystallization inhibitor as mentioned in Mexican Patent MX 231185 and Argentine Patent Application No P000102422. Consequently, it is a simpler industrial elaboration procedure.

The solvents to be used may be organic or mixtures of organic and inorganic solvents. Between the organics, there may be mentioned methylene chloride or ethanol since they are easily removed. Ethanol is the preferred solvent and following removal there is no possibility of presence of contaminating solvents in the pharmaceutical form. As a solvent mixture, ethanol-water and ethanol-methylene chloride are preferred.

The sublingual tablets obtained according to the present invention have the following characteristics.

(a) They are elaborated with the least possible amount of excipients. The decrease in the amount of excipients contributes to the rapid disintegration of the tablet and to a greater interaction between the active principle it contains and the sublingual or buccal mucosa, thereby favoring its absorption.

(b) They have a very small size.

(c) They have a weight lower than 70 mg and preferably between 30 and 40 mg. The final weight of the tablets of the present invention is practically 2- to 6-fold lower than the weight of other conventional oral tablets having the same active principle and concentration.

(d) They have a disintegration time lower than 1 minute and preferably between 8 and 15 seconds following being located in sublingual or buccal position. It is known that the greater the disintegration rate the higher the possibility of absorption of the drug. Thus, for example, USP XXIII requires for isosorbide dinitrate or nitroglycerine sublingual tablets a maximum disintegration time not greater than 2 minutes and for ergotamine tartrate, lower than 5 minutes. Surprisingly, the disintegration time of the sublingual composition of alprazolam by the procedure described in the experimental part of the present application is much less than suggested by USP XXIII for isosorbide dinitrate or nitroglycerine sublingual tablets. It is practically 8 to 15 times less.

It has surprisingly been found that alprazolam present in the sublingual tablet prepared according to the procedure described in the experimental examples dose not completely turn back to crystalline state; or occasionally recovers said crystalline state. This confers the pharmaceutical composition object of the present invention the desired characteristics of solubility and bioavailability. Preferably, the alprazolam active principle comprised in the medicament is in a non-crystalline or partially crystalline form, according to an X-ray diffraction crystallography expanded for the position delta 9-12.5 (2 theta). In the present description and claims, it must be understood that the expression "non-crystalline state" means that it has a content lower than 10%, preferably lower than 5%, of the crystalline state in respect of the total content of alprazolam. Also, when in the present description and claims the expression "alprazolam is not significantly detected in its crystalline form according to X-ray diffraction crystallography expanded for the position delta 9-12.5 (2 theta)" is used, it must be considered to be equivalent to say that there is a content lower than 10%, preferably lower than 5%, of the crystalline state in respect of the total content of alprazolam.

Figure 2:
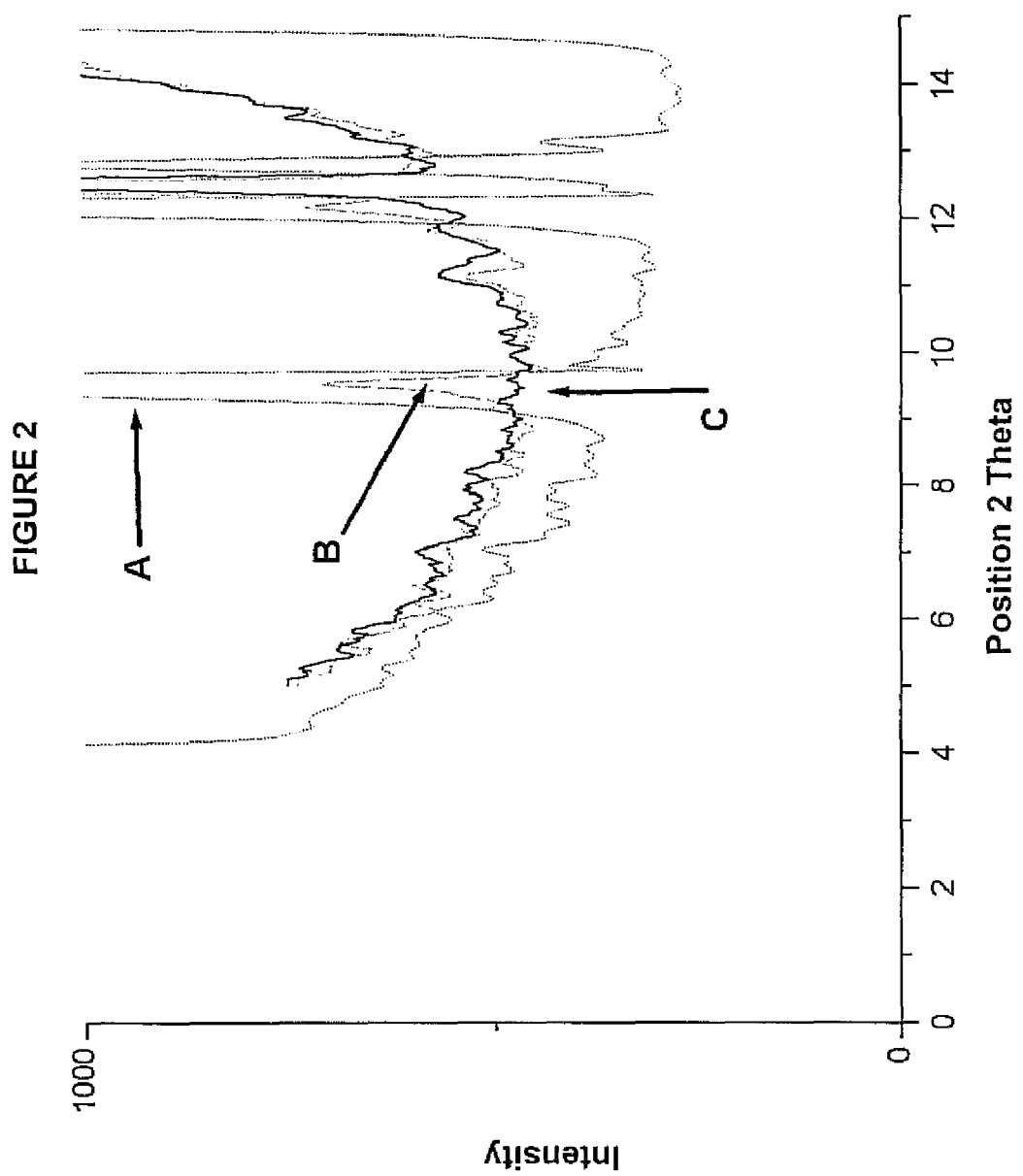
FIG. 2 describes graphs corresponding to the 3 overlapped samples of X-ray diffraction expanded for the position Delta 9-12.5 (2 theta), in the same way as FIG. 1. But in this case Sample C was prepared according to the formula an procedure described in Example 2 of the present invention. Both sample B (physical mixture of all components) and C (ground tablets of the invention) comprise 1 mg alprazolam.
Figure 3:
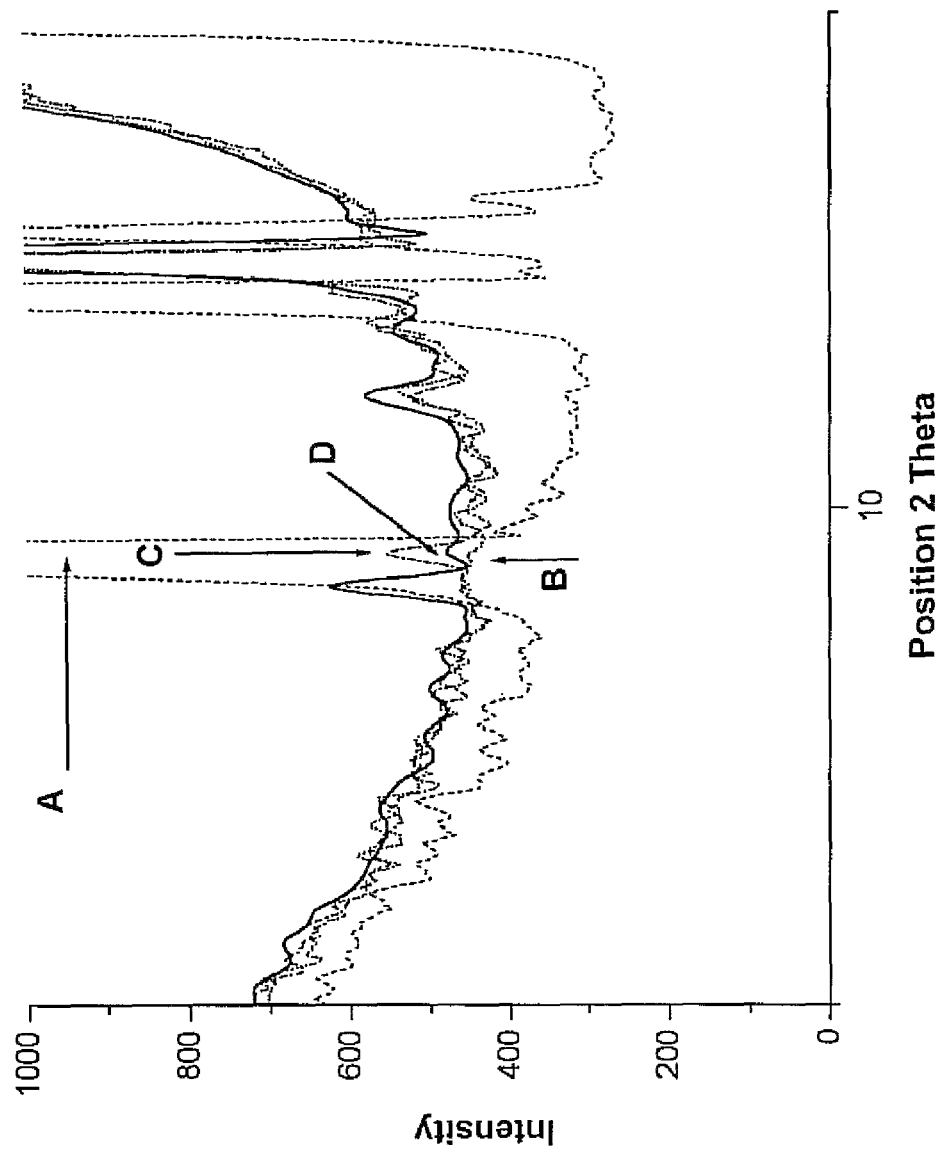
FIG. 3 describes graphs corresponding to the 4 overlapped samples of X-ray diffraction expanded for the position Delta 9-12.5 (2 theta), for tablets containing 0.5 mg alprazolam manufactured by the procedure described in example 1, with a 36-month aging from its elaboration date
Sample A: reference alprazolam, pure crystalline powder.
Sample B: reference of the physical mixture of all components except alprazolam and in the same proportion as used according to what is described in example 1 of the present invention.
Sample C: reference of the physical mixture of all components including alprazolam, in the same proportion as used according to what is described in example 1.

The loss of crystalline state of alprazolam in the sublingual tablets may be observed by comparison of the X-ray spectra described in FIGS. 1-3 of the present invention.

For the assay of the samples a Panalytical X-Ray Diffraction equipment was used, with a K-Cal source, length 1.54184 angstroms (Hardware X-Per pro, X Ray Diffractions Systems; Software X-Per Industry and X-Per High Score).

(Bibliografia: Powder Diffraction File-ICDD; Cambridge Crystallography Data Center; Inorganic Crystal Structure Database).

In FIGS. 1-3 X-ray diffraction graphs are described expanded for the position Delta 9-12.5 (2 theta) corresponding to different overlapped samples.

In FIG. 1, a very intense signal is observed in the position indicated for pure alprazolam. Said signal has diminished intensity as compared to the reference for the physical mixture of all components of the sublingual tablets in the same proportion as used in the elaboration of tablets according to the procedure described in the present invention. Such decrease in intensity is attributable to dilution of alprazolam among the other components in Ia composition (0.5 mg alprazolam in an average weight of 35 mg). Meanwhile, for the sublingual tablets with 0.5 mg alprazolam elaborated according to the procedure of the present invention and ground, no remarkable signal is observed which means evidence of crystallinity of alprazolam.

In FIG. 2, conclusions are similar to those of FIG. 1, but in this case the amount of alprazolam in the physical mixture and in the ground tablets according to the invention is 1 mg. The difference in intensity of signals corresponding to ground sublingual tablets and to the physical mixture is greater in all components of the pharmaceutical composition.

In FIG. 3 a very intense signal can also be observed at the position indicated for the reference of pure alprazolam in crystalline powder form. For the reference of the physical mixture of all components except alprazolam, no signal thereof is observed.

For the reference of the physical mixture of all components containing 0.5 mg alprazolam, a signal of alprazolam is observed with decreased magnitude with respect to the sample of pure alprazolam. Finally, for the sample of ground sublingual tablets with a content of 0.5 mg alprazolam elaborated by the procedure of the present invention and having a 36-month period of aging after manufacturing, no signal is observed attributable to crystalline alprazolam as observed in the above positive references of alprazolam.

Therefore, when sublingual tablets according to the present invention are prepared which have very high disintegration rate as mentioned and alprazolam with little or no crystallinity in the composition, they are particularly suitable for sublingual administration. Also, this characteristic of the pharmaceutical composition contributes to the total "availability" thereof in the buccal cavity in a remarkably short period of time, and therefore assures the absorption of the drug will take place preferably through the sublingual and buccal mucosa. Such absorption is also favored by the indication to the patient to place the tablet under the tongue for the following reasons.

a) Surprisingly, it can be observed that in less than 15 seconds there are practically no particles of significant size at the buccal cavity from the disintegration of the whole tablet that may be easily swallowed and incorporated to the gastrointestinal tract. This would result in higher absorption rate of alprazolam than clinically observed in plasma level studies.

b) Polyvinylpyrrolidone, in particular povidone K-30, incorporated to the tablet further has recognized mucoadhesive properties, which might be connected to the higher absorption rate observed in clinical studies in healthy volunteers against other oral tablets. The presence of a polyvinylpyrrolidone of choice, in particular povidone K-30, in the tablets described in the present invention due to its mucoadhesive activity could:

i) increase the time of contact between alprazolam from the disintegration of the tablet (less than 15 seconds) and the sublingual mucosa, an effect not sought in oral-type tablets;
ii) decrease the passage to the gastrointestinal tract of alprazolam due to deglutition.

Theoretically, both mechanical effects could explain the surprising, remarkable rate of absorption of alprazolam observed for the sublingual tablets of the invention through the clinical studies, wherein a remarkable improvement of 90% was observed of the patients treated with the sublingual tablets containing 0.5 mg alprazolam obtained by the process of the invention in the short-term treatment of insomnia associated to anxiety.

The formulations of the invention exhibit a greater shortening, in statistically significant terms, of the latency time of sleeping, with the same dose of alprazolam, as compared to conventional formulations.

Many epidemiological studies have revealed the high prevalence of sleeping disorders in different cultures and groups of patients. It is thought that about one third of the population will show some kind of sleep dysfunction throughout their lives. This fact has resulted in development of numerous psychometric instruments intended for facilitating diagnosis of this kind of problems. However, many of these instruments lack a suitable validation an only a few of them measure the "quality of sleep". Probably this is because the "quality of sleep" is a complex phenomenon, difficult to define and difficult to measure objectively, in which quantitative-sleep duration, latency of sleep, number of awakenings- and subjective-deepness, reparability-aspects of sleep are integrated.

In 1988 Daniel J. Buysse et al. designed the Pittsburgh Sleep Quality Questionnaire (PSQI) with the purpose of disposing of an instrument that would analyze the quality of sleep and that could be used in clinical trials. (Buysse D J, Reynolds III ChF, Monk T H, Berman S R, Kupfer D J. The Pittsburgh Sleep Quality Index: A New Instrument for Psychiatric Practice and Research. Psychiatry Research 1989; 28:193-213; Royuela A, Macias J A, Moreno P. et al. Estudio de la aplicación del PSQI a pacientes psiquiátricos. Anales de Psiquiatria 1994; Supl 1:10).

Such questionnaire was soon widely used and adopted. In our country, it has been adapted, validated and used in many research works and different groups of patients in the past decade.

PSQI is a brief, simple questionnaire, and it is well accepted by patients. In the general population, it can be used as a screening element for detecting "good" and "bad" sleepers. In a psychiatric population, it may identify patients having a sleep disorder concomitant with their mental process. It is capable of orienting the clinician about the most damaged components of sleep. It allows for monitoring of patients in order to follow the natural history of the sleep disorder they suffer; the influence of the sleep alteration on the course of psychiatric processes; the response to specific treatments, etc.

PSQI is an auto-administered questionnaire consisting of 19 items auto-assessed by the patient and 5 questions assessed by his/her bed-partner. The latter five questions are used as clinical information, but do not contribute to the overall PSQI scoring. The 19 items analyze the different determining factors of the quality of sleep, which are grouped in 7 components: quality of sleep, latency of sleep, sleep duration, sleep efficiency, sleep alterations, use of medication for sleeping and daytime dysfunction. Each component is scored from 0 to 3. From the sum of all 7 components the overall PSQI scoring is obtained, which ranges from 0 to 21 points. The greater the scoring, the poorer the quality of sleep.

The efficacy of alprazolam was assessed in sublingual tablets containing 0.5 mg alprazolam according to the present invention in the short-term treatment versus conventional tablets of 0.5 mg alprazolam (Xanax®, Pfizer) as sleep inductors in disorders thereof in the short-term treatment of insomnia associated with anxiety states.

The study was carried out with 37 patients, of which 22 were women and 15 men, with ages ranging from 21 to 74 years, a median of 53 years and an average of 51 years. Patients incorporated to the trial performed at entry (day 0) a analogue visual scale to insomnia. Said scale was supplemented with an Abbreviated Pittsburgh Sleep Quality Questionnaire (PSQI). On their second visit after completing the first treatment, said patients had to attend a medical consultation, where the PGI (Patients General Impression), the Visual Scale Analogue for Insomnia and the Abbreviated Sleep Quality Questionnaire were assessed. The final visit was carried out at about day 16, once the second scheme of the treatment had been completed, wherein the Visual Scale Analogue for Insomnia, PGI, PSQI and degree of preference of one of the treatments were repeated.

The results obtained are described in Chart I.

As regards the preference for the conventional oral form, it was not associated with a better response but with its lack of flavour, neutral choice due to the fast deglutition of the oral pharmaceutical form and less time in contact with the oral mucous membrane, while the choice of sublingual form of the present invention was associated with the quick action and the quality of the sleep achieved. From the 10 patients who chose the conventional oral form, 6 patients had a lower latency period with the sublingual pharmaceutical form.

94% of the patients observed a significant reduction in the sleep latency with both products, but with the sublingual tablets according to the present invention, this reduction was higher than that caused by the conventional oral tablets in statistically relevant terms ($p<0.01$).

Additionally, an inquiry was made to assess the quality of the sleep, the reduction of the latency time to sleep, and the increased amount of hours to sleep in the short term treatment with alprazolam administered orally in sublingual tablets with 0.25 mg alprazolam according to the present invention. The inquiry was carried out with 18 patients that received sublingual tablets for 1 week. The results are shown in Chart II.

CHART I

| Patient | basal Latency (min.) | Latency c/comp. sublingual* (min.) | Latency W/oral comp.** (min.) | Preference |
|---|---|---|---|---|
| 1 | 30 | 20 | 30 | sublingual |
| 2 | 90 | 15 | 30 | oral |
| 3 | 30 | 30 | 20 | oral |
| 4 | 60 | 30 | 35 | oral |
| 5 | 60 | 30 | 35 | sublingual |
| 6 | 180 | 30 | 20 | sublingual |
| 7 | 60 | 30 | 35 | sublingual |
| 8 | 30 | 30 | 30 | sublingual |
| 9 | 60 | 20 | 15 | oral |
| 10 | 60 | 15 | 20 | sublingual |
| 11 | 60 | 10 | 25 | sublingual |
| 12 | 90 | 15 | 30 | sublingual |
| 13 | 40 | 15 | 25 | sublingual |
| 14 | 40 | 20 | 25 | oral |
| 15 | 90 | 90 | 90 | oral |
| 16 | 180 | 10 | 15 | oral |
| 17 | 60 | 15 | 30 | sublingual |
| 18 | 60 | 10 | 25 | sublingual |
| 19 | 45 | 15 | 25 | sublingual |
| 20 | 120 | 15 | 30 | sublingual |
| 21 | 20 | 10 | 10 | sublingual |
| 22 | 150 | 15 | 45 | sublingual |
| 23 | 90 | 15 | 15 | sublingual |
| 24 | 180 | 15 | 30 | sublingual |
| 25 | 25 | 10 | 25 | sublingual |
| 26 | 210 | 45 | 180 | sublingual |
| 27 | 10 | 10 | 10 | sublingual |
| 28 | 90 | 20 | 30 | either |
| 29 | 60 | 10 | 10 | sublingual |
| 30 | 30 | 15 | 15 | oral |
| 31 | 40 | 15 | 15 | sublingual |
| 32 | 45 | 25 | 60 | sublingual |
| 33 | 180 | 30 | 40 | sublingual |
| 34 | 120 | 20 | 30 | sublingual |
| 35 | 30 | 25 | 30 | oral |
| 33 | 60 | 30 | 40 | sublingual |
| 37 | 120 | 20 | 30 | sublingual |

*alprazolam sublingual tablets according to the present invention.
**conventional alprazolam oral tablets.

In Chart I, it can be seen that both treatments were equally efficient for insomnia associated with anxiety. As regards preference, 26 patients (70.3%) choose sublingual tablets according to the present invention, 10 patients (27%) preferred the conventional oral form and one patient (2.7%) did not have any preferences.

CHART II

| Alprazolam sublingual tablets 0.25 mg | | | | | |
|---|---|---|---|---|---|
| Patient | Previous Lat. | Post. Lat. | Previous Hs. | Post. Hs. | Dose |
| 1. | 30' | 15' | 5.30 hs | 7 hs | 1 |
| 2. | 120' | 10' | 5 hs | 7 hs | 1 |
| 3. | 60' | 15' | 4 hs | 7 hs | 2 |
| 4. | 45' | 15' | 5 hs | 7 hs | 1 |
| 5. | 50' | 15' | 3 hs | 6 hs | 1 |
| 6. | 60' | 20' | 7 hs | 7 hs | 2 |
| 7. | 90' | 20' | 4 hs | 6:30 hs | 1 |
| 8. | 10' | 10' | 7 hs | 7 hs | 1 |
| 9. | 60' | 30' | 4 hs | 7 hs | 2 |
| 10. | 60' | 30' | 4 hs | 7 hs | 2 |
| 11. | 90' | 30' | 4 hs | 7 hs | 2 |
| 12. | 90' | 30' | 4 hs | 7 hs | 2 |
| 13. | 60' | 30' | 4 hs | 7 hs | 1 |
| 14. | 90' | 30' | 5 hs | 7 hs | 1 |
| 15. | 60' | 30' | 4 hs | 5:30 hs | 1 |
| 16. | 120' | 30' | 4 hs | 8 hs | 1 |
| 17. | 60' | 30' | 4 hs | 6 hs | 2 |
| 18. | 120' | 30' | 4 hs | 6 hs | 1 |

As can be seen in Chart II, 60% of the patients required only one tablet to sleep while 40% of the patients needed 2 sublingual tablets. In 95% of the cases, the latency to sleep was reduced to half or less the time prior to the treatment $p<0.01$. 100% of the patients improved their quality of sleep and 95% of the patients slept 40% or more time with the treatment.

Consequently, alprazolam administered in sublingual tablets in doses of 0.5 mg according to the present invention showed to be more effective for a short-term treatment than when administered the same amount of alprazolam but in the conventional oral form.

Likewise, the quality of sleep improved in the treatment in the short term treatment with alprazolam administered by sublingual tablets of 0.25 mg of dose according to the present invention.

The pharmaceutical composition also showed to be useful as an anxiolytic and in the treatment of panic disorder, especially in the panic crisis due to its quick action.

The sublingual or buccal tablets have a little size and a considerable disintegration rate. This allows them to be used at any time and place, therefore these do not require the use of water or other beverages to assist in their administration.

The following non limiting examples show in practice the compositions and preparation processes of the present invention.

EXAMPLE 1

Formula for 10,000 sublingual or buccal tablets of 0.5 mg alprazolam

| | |
|---|---|
| Alprazolam | 5 g |
| Cross-linked carboxymethylcellulose | 3.5 g |
| Flavoring | q.s. |
| Lactose | 82 g |
| Povidone | 3.5 g |
| Sodium Stearyl Fumarate | 3.5 g |
| Microcrystalline Cellulose q.s. | 350 g |

5 g alprazolam were dissolved in 130 g of ethanol to prepare 10,000 tablets. Then, 3.5 g povidone were dissolved in this solution.

0.875 g cross-linked carboxymethylcellulose (25% of the formula) and the indicated amounts of microcrystalline cellulose and lactose were placed in the container of a high speed mixer-granulator. This was stirred and then the binding liquid was added to the powder mixture until a consistent granule was formed. The granulate was dried in a fluid circulating bed drier until the solvent was removed.

The dried granulate was calibrated in a conical sieve mill until a uniform particle size was obtained. The granulate obtained was added to a container. The flavorings were added, as well as 75% of the amount calculated of cross-linked carboxymethylcellulose, all of them were calibrated previously in the same manner, then dried in the type V mixer during 20 minutes. The indicated amount of sodium stearyl fumarate was added, and it was stirred during 5 minutes. Then, compression was performed in a rotating compressor.
Determinations:
  Weight: 35 mg
  Disintegration time (USP Apparatus): less than 30 seconds.
  Medium: Water. Without discs.
  Friability: Less than 0.5%
  Hardness: between 2 and 4 SC.

EXAMPLE 2

Formula for 10,000 sublingual or buccal tablets of 1 mg alprazolam

| | |
|---|---|
| Alprazolam | 10 g |
| Cross-linked carboxymethylcellulose | 3.5 g |
| Flavorings | q.s. |
| Lactose | 82 g |
| Povidone | 3.5 g |
| Sodium stearyl fumarate | 3.5 g |
| Mycrocrystalline cellulose q.s. | 350 g |

To prepare 10,000 tablets 10 g alprazolam were dissolved in 180 g ethanol. In this solution was dissolved 3.5 g of povidone.

0.875 g of cross-linked carboxymethylcellulose (25% of the formula) and the indicated amounts of microcrystalline cellulose and lactose were placed in the container of a high speed mixer-granulator. This was stirred and then the binding liquid was added to the powder mixture until a consistent granule was formed. The granulate was dried in a fluid circulating bed drier until the solvent was removed.

The dried granulate was calibrated in a conical sieve mill until a uniform size of particle was obtained. The obtained granulate was added to a container. The flavorings were added, as well as 75% of the amount calculated of cross-linked carboxymethylcellulose, all of them were previously calibrated in the same manner, then dried in the type V mixer during 20 minutes. The indicated amount of sodium stearyl fumarate was added, and it was stirred during 5 minutes. Then, compression was performed in a rotating compressor.
Determinations:
  Weight: 35 mg
  Disintegration time (USP Apparatus): Less than 30 seconds.
  Medium: Water. Without discs.
  Friability: Less than 0.5%
  Hardness: Between 2 and 4 SC.

EXAMPLE 3

Formula for 10,000 sublingual or buccal tablets of 0.25 mg alprazolam

| | |
|---|---|
| Alprazolam | 2.5 g |
| Cross-linked carboxymethylcellulose | 3.5 g |
| Flavorings | q.s. |
| Lactose | 82 g |
| Povidone | 3.5 g |
| Sodium stearyl fumarate | 3.5 g |
| Mycrocrystalline cellulose q.s. | 350 g |

2.5 g alprazolam was dissolved en 130 g ethanol to prepare 10,000 tablets. In this solution, 3.5 g povidone was dissolved.

0.875 g cross-linked carboxymethylcellulose (25% of the formula) and the indicated amounts of microcrystalline cellulose and lactose were placed in the container of a high speed mixer-granulator. This was stirred and then the binding liquid was added to the powder mixture until a consistent granule was formed. The granulate was dried in a fluid circulating bed drier until the solvent was removed.

The dried granulate was calibrated in a conical sieve mill until a uniform size of particle was obtained. The obtained granulate was added to a container. The flavorings were added, as well as 75% of the amount calculated of cross-linked carboxymethylcellulose, all of them were previously calibrated in the same manner, then dried in the type V mixer during 20 minutes. The indicated amount of sodium stearyl fumarato was added, and it was stirred during 5 minutes. Finally, compression was performed in a rotating compressor.
Determinations:
  Weight: 35 mg
  Disintegration time (USP Apparatus): Less than 30 seconds.
  Medium: Water. Without discs.
  Friability: Less than 0.5%
  Hardness: Between 2 and 4 SC.

EXAMPLE 4

In this test, 3 batches of sublingual tablets including 0.5 mg alprazolam were prepared according to the procedure described in Example 1, and the uniformity of the contents as well as the stability of the tablets were analyzed.

a) Uniformity of the Contents

To determine the uniformity of the contents, the samples were analyzed by high pressure liquid phase chromatography (HPLC) according to the procure described in the stability studies according to Pharmacopeia USP 29, General method <905>. The maximum variation coefficient coded must not be higher than 6%.

The results obtained for the three batches are the following:

Batch 1:

Vc. (variation coefficient): 2.2%

N (number of tablets tested)=10

Batch 2:

Vc (variation coefficient): 1.7%

N (number of tablets tested)=10

Batch 3:

Vc (variation coefficient): 1.8%

N (number of tablets tested)=10

According to the reported data, the 3 batches of 0.5 mg alprazolam sublingual tablets made according to the procedure of Example 1 comply with the general specifications for tables stated in Pharmacopeia USP.

b) Stability

Stability studies were carried out for the same samples (Batches 1, 2, and 3) made according to the procedure of Example 1. For the stability analysis, the alprazolam content in the 0.5 mg alprazolam sublingual tablets made according to the procedure of Example 1 was evaluated at different times of the 24-month storage period by HPLC; additionally, disintegration tests were carried out according to Pharmacopeia USP.

For the evaluation by means of HPLC, 10 sublingual tablets were taken and transferred to corresponding 25 ml flasks. 20 ml mobile phase were added and stirred with ultrasound during 20 minutes. These were completed to volume with mobile phase, then homogenized and stirred an additional 10 minutes. They were allowed to decant and then filtered with a 0.45 micron nylon membrane filter, discarding the initial 3 ml of the filtrate.

A high-pressure liquid phase chromatograph was used, equipped with an ultraviolet light and a diode array. The column was filled with silica microparticles chemically bonded to octadecylsylane Rp-18 (3-5µ). The mobile phase used was a phosphate buffer solution, pH=6.0:Acetonitrile:Tetrahydrofuran (55:40:5), the phosphate buffer solution pH=6.0, was prepared dissolving 8.0 g $PO_4H_2K$ and 2.0 g $PO_4K_2H$ in 1000 ml of water and it was adjusted to pH=6.0, if necessary, with dilute phosphoric acid or dilute potassium hydroxide. The working temperature was 40° C. with a flow rate: 1 ml/min.

10 microliter injections were carried out as sample. The alprazolam detection was effected by radiation with ultraviolet light at 220 nm; and the quantitation was carried out by means of an electronic integration of the peak area corresponding to alprazolam. The chromatographic system to be applied must comply with the adequacy parameters requiring that the relative standard deviation (SD %) of 5 (five) injections of a reference solution must be ≤2.0%.

Specifications

The specifications required according to Pharmacopeia USP are that disintegration must be within 30 seconds and the tables must include not less than 90% the amount stated of alprazolam after the storage period.

The samples were packed in PVC (250) and printed aluminium blisters, and then stored at a temperature of 30° C.±2° C., with a humidity content of 70%±5% RH.

Percent alprazolam is calculated by the following formula $$\% \text{ Alprazolam} = \frac{Am}{Fr} 10 \times \frac{Pp}{Pm}$$

wherein:

Am=peak area of alprazolam in the sample.

Fr=average response factor for alprazolam in references.

Pp=average weight (mg).

Pm=sample weight taken for the test (mg).

Results

The results obtained after 6, 12, 18, 24, and 43 months, for the same 3 batches of alprazolam tablets made according to example 1, are described in the following Table I.

TABLE I

| | PERIOD (MONTHS) | | | | | |
|---|---|---|---|---|---|---|
| Batch 1 | 0 | 6 | 12 | 18 | 24 | 43 |
| | | 5 | 4 | 9 | 5 | 7 |
| ASSAY (% of the stated value) | 100.3 | 97.8 | 100.4 | 100.8 | 99.6 | 102.4 |

| | PERIOD (MONTHS) | | | | | |
|---|---|---|---|---|---|---|
| Batch 2 | 0 | 7 | 12 | 18 | 25 | 37 |
| DISINTE-GRATION (sec) | 15 | 6 | 9 | 6 | 6 | 6 |
| VALUE (% of the stated value) | 101.0 | 98.0 | 98.4 | 97.8 | 97.5 | 95.2 |

| | PERIOD (MONTHS) | | | | |
|---|---|---|---|---|---|
| Batch 3 | 0 | 5 | 11 | 18 | 24 |
| DISINTE-GRATION (sec) | 16 | 7 | 6 | 5 | 7 |
| VALUE (% of the stated value) | 100.0 | 98.6 | 98.0 | 100.4 | 99.0 |

The experimental results obtained with the 3 batches made according to example 1 show a disintegration time lower than 30 seconds and the alprazolam contents obtained in the three cases was higher than 95% of each original pharmaceutical preparation. Therefore, alprazolam sublingual tablets meet the following requirements:

1) Content Uniformity (according to Pharmacopeia USP 29)

2) Disintegration time: less than 30 seconds (according to Pharmacopeia USP 29)

3) Stability according to the general guidelines ICH

The principles, preferred embodiments and ways of carrying out the present invention have been described in the above specification. However, it must be understood that the present invention is not limited to the particular embodiments herein described since these are intended to be illustrative and not limiting. Variations and modifications may be performed by those skilled in the art without departing from the spirit of the present invention.

The invention claimed is:

1. A pharmaceutical composition in the form of sublingual tablets characterised by:

comprising combination of alprazolam and a binder having mucoadhesive properties; wherein the ratio of alprazolam to the binder is in the range between 0.3:1 and 3:1; and, wherein said composition has a disintegration time lower than 30 seconds, in vitro when measured in a standard USP apparatus in medium water without discs according to the United States Pharmacopoeia; and wherein the degree of crystallinity of the alprazolam is less than 10%.

2. The pharmaceutical composition according to claim 1, wherein said composition has a disintegration time lower than 15 seconds, in vitro when measured in a standard USP apparatus in a water medium without discs according to the United States Pharmacopoeia.

3. The pharmaceutical composition of claim 1 wherein the binder is polyvinylpyrrolidone.

4. The pharmaceutical composition of claim 3 wherein each of said tablets comprises between 0.1 and 2 mg of alprazolam.

5. The pharmaceutical composition of claim 3 wherein each of said tablets comprises between 0.2 and 1.2 mg of alprazolam.

6. The pharmaceutical composition of claim 3 wherein each of said tablets comprises between 0.4 and 0.6 mg of alprazolam or between 0.9 and 1.1 mg of alprazolam.

7. The pharmaceutical composition according to claim 3 characterised in that each of said tablets comprises 0.5 mg of alprazolam.

8. The pharmaceutical composition according to claim 3 characterised in that each of said tablets comprises 1.0 mg of alprazolam.

9. The pharmaceutical composition according to claim 1, wherein each of said tablets has a weight lower than 40 mg.

10. The pharmaceutical composition according to claim 9, wherein the weight of each of said tablets is 35 mg.

11. A process for preparing a pharmaceutical composition comprising alprazolam in the form of sublingual tablets according to claim 1, wherein said preparation procedure comprises the following steps:

dissolving alprazolam and a binder in a pharmaceutically acceptable solvent to form a solution;

providing a mixture comprising a first portion of cross-linked carboxymethyl-cellulose;

impregnating said mixture with said solution so as to form a granular mass;

drying the above granular mass and grinding until uniform granularity is achieved;

adding a second portion of cross-linked carboxymethyl-cellulose and flavoring additives to the dry mass, then mixing and compressing.

12. The pharmaceutical composition according to claim 1, wherein the degree of crystallinity of the alprazolam is less than 5%.

* * * * *